United States Patent
Clendennen et al.

(10) Patent No.: US 10,767,199 B2
(45) Date of Patent: Sep. 8, 2020

(54) ENZYMATIC PREPARATION OF PROPAMOCARB

(71) Applicant: Eastman Chemical Company, Kingsport, TN (US)

(72) Inventors: Stephanie Kay Clendennen, Kingsport, TN (US); Neil Warren Boaz, Kingsport, TN (US); Jean-Michel Rabasse, Paris (FR)

(73) Assignee: Eastman Chemical Company, Kingsport, TN (US)

(*) Notice: Subject to any disclaimer, the term of this patent is extended or adjusted under 35 U.S.C. 154(b) by 0 days.

(21) Appl. No.: 16/344,631

(22) PCT Filed: Oct. 25, 2017

(86) PCT No.: PCT/US2017/058217
§ 371 (c)(1),
(2) Date: Apr. 24, 2019

(87) PCT Pub. No.: WO2018/081221
PCT Pub. Date: May 3, 2018

(65) Prior Publication Data
US 2019/0300916 A1    Oct. 3, 2019

(30) Foreign Application Priority Data

Oct. 31, 2016 (EP) .................... 16306431

(51) Int. Cl.
*C12P 13/00* (2006.01)
*C12N 9/20* (2006.01)
*C12P 13/02* (2006.01)

(52) U.S. Cl.
CPC .............. *C12P 13/001* (2013.01); *C12N 9/20* (2013.01); *C12P 13/02* (2013.01); *C12Y 301/01003* (2013.01)

(58) Field of Classification Search
None
See application file for complete search history.

(56) References Cited

U.S. PATENT DOCUMENTS

| | | |
|---|---|---|
| 5,677,307 A | 10/1997 | Gesing et al. |
| 5,760,067 A | 6/1998 | Jautelat et al. |
| 5,807,877 A | 9/1998 | Lantzsch et al. |
| 5,843,978 A | 12/1998 | Wernthaler et al. |
| 5,985,903 A | 11/1999 | Assmann et al. |
| 6,054,476 A | 4/2000 | Seitz et al. |
| 6,114,374 A | 9/2000 | Lieb et al. |
| 6,339,103 B1 | 1/2002 | De'Ath et al. |
| 6,589,974 B1 | 7/2003 | Heinemann et al. |
| 6,639,097 B1 | 10/2003 | De'Ath et al. |
| 6,806,292 B2 | 10/2004 | Riebel et al. |
| 8,206,969 B2 | 6/2012 | Hauer et al. |
| 10,035,995 B2 | 7/2018 | Clendennen et al. |
| 2013/0023028 A1 | 1/2013 | Svendsen et al. |

FOREIGN PATENT DOCUMENTS

| | | |
|---|---|---|
| EP | 1 254 894 A1 | 11/2002 |
| EP | 2 522 736 A1 | 11/2012 |
| WO | WO 02/090322 A1 | 11/2012 |

OTHER PUBLICATIONS

Papavizas, G. C., et al.; Fungistatic Activity of Propyl-N-(γ-dimethylaminopropyl) carbamate on *Pythium* spp. and its Reversal by Sterols; Phytopathology 68: 1667-1671.
Kreutzberger, Charles B.; "Chloroformates and Carbonates"; Kirk-Othmer Encyclopedia of Chemical Technology, vol. 6, 2003, pp. 290-323.
Ma, Qingxiang, et al.; "Synthesis of dipropyl carbonate over calcined hydrotalcite-like compounds containing La"; Applied Catalysis A: General 464-465; (2013), pp. 142-148.
Pesticide Synthesis Handbook, Thomas A. Unger, (1996), p. 94.
Safety Data Sheet; "Propyl Chloroformate"; Revision Date Feb. 10, 2015.
Busto, Eduardo, et al.; "First Desymmetrization of 1,3-Propanediamine Derivatives in Organic Solvent. Development of a New Route for the Preparation of Optically Active Amines"; Organic Letters, vol. 9 No. 21, (2007), pp. 4203-4206.
Notification of Transmittal of The International Search Report and The Written Opinion of The International Searching Authority, of the Declaration; International Application No. PCT/US2017/058217 with a filing date of Oct. 25, 2017.
Arora, Benu et al.; "Enzyme promiscuity: using the dark side of enzyme specificity in white biotechnology"; Sustainable Chemical Processes; (2014) 2:25.
Hult, Karl et al.; "Enzyme promiscuity: mechanism and applications"; Trends in Biotechnology, vol. 25 No. 5.
Xie, Yuan, et al.; "Enhanced Enzyme Kinetic Stability by Increasing Rigidity within the Active Site"; The Journal of Biological Chemistry (2014), vol. 289, No. 11: pp. 7994-8006.
Hughes, Stephen R., et al.; "Synthetic resin-bound truncated *Candida antarctica* lipase B for production of fatty acid alkyl esters by transesterification of corn and soybean oils with ethanol or butanol"; Journal of Biotechnology 159 (2012), pp. 69-77.
Lie, Danni, et al.: "Rational Design of Pseudozyma Antarctica Lipase B Yielding a General Esterification Catalyst"; ChemBioChem (2010), 11, pp. 789-795.
Qian, Zhen, et al.; "Structural redesign of lipase B from *Candida antarctica* by circular permutation and incremental truncation"; J. Mol. Biol., (2009); 393 (1): pp. 191-201.
Skjot, Michael, et al.; "Understand the Plasticity of the α/β Hydrolase Fold: Lid Swapping on the *Candida antarctica* Lipase B Results in Chimeras with Interesting Biocatalytic Properties"; ChemBioChem, (2009), 10, pp. 520-527.

(Continued)

Primary Examiner — Paul J Holland
(74) Attorney, Agent, or Firm — Robert C. Morriss; Kenrick L. Vidale

(57) ABSTRACT

A process for preparing Propamocarb is presented. The preparation of Propamocarb (propyl 3-(dimethylamino)propylcarbamate) from 3-dimethylaminopropylamine and dipropyl carbonate is performed using an enzyme catalyst. In certain embodiments, the catalyst is a lipase enzyme, immobilized on a solid support. Advantages of the process include the avoidance of the use of chloroformate or vinyl carbonate.

7 Claims, No Drawings

(56) References Cited

OTHER PUBLICATIONS

Kapoor, Manali, et al.; "Lipase promiscuity and its biochemical applications"; Process Biochemistry, 47, (2012), pp. 555-569.
Giuseppe, Manco, et al.; "Enzyme Promiscuity in the Hormone-sensitive Lipase Family of Proteins"; Protein & Peptide Letters, 2012, 19, pp. 144-154.
Babtie, Ann, et al.; "What makes an enzyme promiscuous?"; Current Opinion in Chemical Biology, 2010, 14: pp. 200-207.
Khersonsky, Olga, et al.; "Enzyme promiscuity: evolutionary and mechanistic aspects"; Current Opinion in Chemical Biology 2006, 10: pp. 498-508.
Wu, Qi, et al.; "Enzymatic Promiscuity for Organic Synthesis and Cascade Process"; Current Organic Chemistry, 2010, 14, pp. 1966-1988.

ENZYMATIC PREPARATION OF PROPAMOCARB

CROSS-REFERENCE TO RELATED APPLICATION(S)

This application is a national stage filing under 35 USC § 371 of International Application Number PCT/US2017/058217, filed on Oct. 25, 2017, which claims the benefit of the filing date to European Application EP16306431.4 filed on Oct. 31, 2016, the entire disclosures of which are incorporated by reference herein.

FIELD OF THE INVENTION

This invention relates to the preparation of Propamocarb from dimethylaminopropylamine and dipropyl carbonate using an enzyme catalyst.

BACKGROUND OF THE INVENTION

This invention relates to the preparation of propamocarb from dimethylaminopropylamine and dipropyl carbonate using an enzyme catalyst. Propyl 3-(dimethylamino)propylcarbamate or Propamocarb (CAS Registry Number: 24579-73-5) is a systemic fungicide used in agriculture and horticulture on a wide variety of plants species (Papvizas et al., 1978, Phytopathology vol. 68 p. 1667-71).

The hydrochloride salt of Propamocarb is marketed under the trademark Previcur™ by Bayer CropScience. Propamocarb can be further derivatized to form the broad-spectrum fungicide dimethyl-[3-(propoxycarbonylamino)propyl]ammonium O-ethylphosphonate (See U.S. Pat. No. 6,339,103). Propamocarb can be further derivatized to form the broad-spectrum fungicides dimethyl[3-(propoxycarbonylamino)propyl]ammonium phosphate and dimethyl-[3-(propoxycarbonylamino)propyl]ammonium phosphite.

The existing synthetic route combines 3-dimethylaminopropylamine (DMAPA) and propyl chloroformate to produce Propamocarb (See p. 94, Pesticide Synthesis Handbook, Thomas A Unger, 1996). The reaction can be performed in an inert organic solvent such as toluene or in water, though higher product yields have been demonstrated using propanol as a solvent (See EP 1 254 894 A1).

Chloroformates are produced by the reaction of phosgene with alcohols or phenols. Hydrogen chloride is evolved during the reaction and is collected in a tower with recovered excess phosgene (See Kreutzberger, C. B. 2003. Chloroformates and Carbonates. Kirk-Othmer Encyclopedia of Chemical Technology). Chloroformates are highly toxic when inhaled. The AEGL-3 value for propyl chloroformate for a 10-minute exposure is 20 ppm in air, meaning exposures at or above that level could lead to life-threatening health effects. There is thus a need for a route to Propamocarb and its derivatives that avoids toxic intermediates such as chloroformates.

BRIEF SUMMARY OF THE INVENTION

The invention is as set forth in the appended claims. Briefly, the invention provides a process for the preparation of Propamocarb which comprises reacting dipropyl carbonate with 3-dimethylaminopropylamine (DMAPA) in the presence of an enzyme catalyst. Surprisingly, the reaction very specifically yields the desired carbamate as the reaction product, and propanol as the only by-product.

One advantage of the process is that a chloroformate or vinyl carbonate is not required as a starting material. Another advantage is that the n-propanol by-product is readily removed from the reaction by distillation. Another advantage is that the presence of an inert solvent is not required. Dipropyl carbonate can be synthesized from dimethyl carbonate and propanol.

DETAILED DESCRIPTION

In one embodiment, the invention provides a process for the preparation of propamocarb which comprises contacting dipropylcarbonate with 3-dimethylaminopropylamine (DMAPA) in the presence of an enzyme catalyst. In another embodiment, the invention provides a process for preparing propyl 3-(dimethylamino)propylcarbamate, which comprises contacting dipropylcarbonate with 3-dimethylaminopropylamine in the presence of at least one enzymatic catalyst, wherein said catalyst comprises a lipase enzyme.

Surprisingly, the reaction very specifically yields the desired carbamate as the reaction product, and propanol as the only by-product. In the absence of the enzyme catalyst, there is very little product formed.

The reaction rate can be modified by methods such as increasing catalyst amount or specific activity, altering reaction pressure, temperature or solvent, altering reactant stoichiometry, and removal of reaction by-products. In one embodiment, the reaction is performed below the boiling point of either reactant (i.e., less than 132° C.); in other embodiments, at a temperature of between 20° and 130° C.; at a temperature of 30° to 100° C.; or 40° to 90° C.

In the present invention, an enzyme is used to catalyze the reaction between dipropylcarbonate with 3-dimethylaminopropylamine. In certain embodiments the enzymatic catalysts include, but are not limited to: hydrolase, esterase, lipase, acylase and protease enzymes. Moreover, within each class of enzyme it is known that there are various types or sources of each enzyme. For example, it is known lipase may be a *Pseudomonas fluorescens* lipase, *Pseudomonas capecia* lipase, Porcine pancreatic lipase, *Candida antarctica* lipase A, *Candida antarctica* lipase B, *Thermomyces lanuginosus* lipase, *Candida rugosa* lipase, and *Mucor miehei* lipase. Galactosidase can be obtained from *Escherichia coli*, *Bacillus* sp., *Kluyveromyces* sp. and *Aspergillus* sp., to name a few. In one embodiment, the enzymes are lipases. These lipases may be in the form of whole cells, isolated enzymes, or enzymes immobilized on supports. Non-limiting examples of commercially available immobilized lipases include but are not limited to Lipase PS (from *Pseudomonas* sp), Lipase PS-C (from *Pseudomonas* sp immobilized on ceramic), Lipase PS-D (from *Pseudomonas* sp immobilized on diatomite), Lipase PS-IM (from *Pseudomonas* sp immobilized on diatomaceous earth), Lipoprime 50T, Novozym® 40086, Lipozyme® TL IM, or Novozym® 435 (lipase B from *Candida antarctica* immobilized on acrylic resin from Novozymes), CalB Immo Plus (Purolite). In certain embodiments, the enzyme catalyst is present in a batch reaction at from 0.01 to 50 weight percent of the reactants, from 0.1 weight percent to 20 weight percent, and from 1 to 10 weight percent.

In one embodiment, the enzyme catalyst is immobilized on a carrier substrate. Suitable materials include organic and inorganic materials such as, for example, carbon such as activated carbon, graphene oxide and carbon nanotubes; inorganic materials such as glass, glass wool, silica gel, metal oxides, clay, diatomaceous earth, iron oxide, and magnetic beads; natural polymeric materials and modified natural polymers such as calcium alginate, glyoxyl agarose, chitosan, gelatin, cellulose, cellulose esters, carboxymethylcellulose, silk, wool, cotton fibers, and coconut fibers; synthetic polymeric materials such as polyethylene, polypropylene, poly(ethylene glycol), polystyrene, polyamide, polyacrylamide, poly(acrylonitrile), poly(phenylendediamine), poly(ethyleneimine), polyvinyl alcohol, polyvinyl chloride, poly(ether sulfone), phenol-formalin resin, acrylic resin, fluoropolymers, anionic exchange resin, cationic exchange resin, epoxy-activated supports, amino-activated supports, octadecyl-activated supports, including copolymers, blends, composites and combinations of any of the above.

In another embodiment, the carrier substrate is selected from a synthetic polymeric material having porosity as the physical form, for example, porous polyethylene, porous polypropylene, porous phenol formalin resin, porous fluoropolymer, porous acrylic resin and porous polystyrene, including copolymers, composites and blends, are more utilized. In the present invention, various immobilizing carriers other than above may also be used so long as they do not hinder the development of the enzymatic reactivity. As a method of immobilizing the thermostable enzyme as described above, any of the methods known in the art of carrier bonding, crosslinking and inclusion may be used.

The process may be carried out in a batch or continuous mode, without solvent or in an inert solvent chosen from cyclic or acyclic ether solvents such as diethyl ether, diisopropyl ether, tert-butyl methyl ether, or tetrahydrofuran, aromatic hydrocarbons such as benzene, toluene, or xylene, aliphatic or alicyclic saturated or unsaturated hydrocarbons such as hexane, heptane, cyclohexane, or limonene, halogenated hydrocarbons such as dichloromethane, dichloroethane, dibromoethane, tetrachloroethylene, or chlorobenzene, polar aprotic solvents such as acetonitrile, dimethyl formamide, or dimethyl sulfoxide, or mixtures thereof. In one aspect, no solvent is used. In another aspect, heptane is used as the solvent. In one aspect the solvent forms an azeotrope with the propanol produced by the reaction, thus facilitating removal of the alcohol from the reaction mixture and driving the reaction mixture to higher conversions.

The present invention includes and expressly contemplates any and all combinations of embodiments, features, characteristics, parameters, and/or ranges disclosed herein. That is, the invention may be defined by any combination of embodiments, features, characteristics, parameters, and/or ranges mentioned herein. As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

The content of all documents cited herein, including patents as well as nonpatent literature, is hereby incorporated by reference in their entirety. To the extent that any incorporated subject matter contradicts with any disclosure herein, the disclosure herein shall take precedence over the incorporated content.

This invention can be further illustrated by the following examples of certain embodiments thereof, although it will be understood that these examples are included merely for purposes of illustration and are not intended to limit the scope of the invention unless otherwise specifically indicated.

The invention is further illustrated in the following examples.

EXAMPLES

Example 1

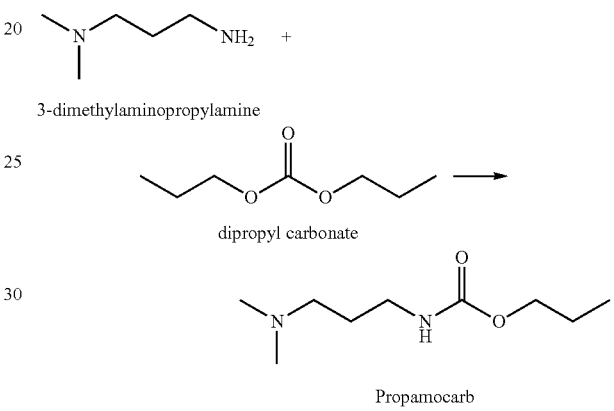

Combine in a 3 dram glass vial:
1.02 g (10 mmoles) 3-dimethylaminopropylamine (DMAPA, Taminco)
1.46 g (10 mmoles) dipropyl carbonate (Aldrich 294934)
60 mg Novozym™ 435 immobilized lipase from Novozymes The reaction was sampled periodically to determine conversion to product (propamocarb) by NMR.

The yield was based on the mol % conversion of DMAPA to the carbamate.

| Time h | Temp °C. | % Non-enzymatic conversion | % Enzymatic conversion |
|--------|----------|----------------------------|------------------------|
| 0      | 25       | 0                          | 0                      |
| 1      | 25       | 0                          | 1                      |
| 2      | 50       | 0                          | 2                      |
| 6      | 50       |                            | 9                      |
| 25     | 50       |                            | 25                     |
| 49     | 70       |                            | 72                     |
| 70     | 70       | 12                         | 91                     |
| 100    | 70       |                            | 98                     |

Then enzymatic reaction was filtered and the solid enzyme was washed with acetone. The volatiles were removed in vacuo to afford 1.55 g (82% yield) of propyl (3-dimethylamino)carbamate as a yellow oil.

$^1$H NMR (CDCl$_3$) d 5.51 (br s, 1H); 4.00 (m, 2H); 3.23 (m, 2H); 2.33 (t, 2H, J=6.8 Hz); 2.21 (s, 6H); 1.65 (m, 4H); 0.93 (m, 3H).

Example 2

Combine in a 3 dram glass vial:
1.02 g (10 mmoles) 3-dimethylaminopropylamine (DMAPA, Taminco)
1.46 g (10 mmoles) dipropyl carbonate (Aldrich 294934)
100 mg of *Candida antarctica* lipase immoblized on an acrylic support (Lewitat® VP OC 1600 from Lanxess).

The reaction was heated to 70° C. and sampled periodically to determine conversion to product (propamocarb) by NMR.
The yield was based on the mol % conversion of DMAPA to the carbamate.

| Time h | % Non-enzymatic conversion | % Enzymatic conversion |
|---|---|---|
| 0 | 0 | 0 |
| 31 | nd | 49 |
| 69 | 19 | 82 |
| 126 | 43 | 97 |

Example 3

Combine in a 3 dram glass vial:
1.02 g (10 mmoles) 3-dimethylaminopropylamine (DMAPA, Taminco)
1.46 g (10 mmoles) dipropyl carbonate (Aldrich 294934)
50 cm$^2$ of *Candida antarctica* lipase immoblized on a porous fluoropolymer support.

The reaction was heated to 70° C. and sampled periodically to determine conversion to product (propamocarb) by NMR.
The yield was based on the mol % conversion of DMAPA to the carbamate.

| Time h | % Non-enzymatic conversion | % Enzymatic conversion |
|---|---|---|
| 0 | 0 | 0 |
| 31 | nd | 35 |
| 69 | 19 | 58 |
| 126 | 43 | 72 |

The invention has been described in detail with particular reference to certain embodiments thereof, but it will be understood that variations and modifications can be effected within the spirit and scope of the invention.

We claim:

1. A process for preparing propyl-3-(dimethylamino)propylcarbamate comprising contacting dipropylcarbonate with 3-dimethylaminopropylamine in the presence of at least one enzymatic catalyst, wherein said catalyst comprises a lipase enzyme.

2. The process of claim 1, wherein the lipase enzyme is selected from the group consisting of *Pseudomonas fluorescens* lipase, *Pseudomonas capecia* lipase, Porcine pancreatic lipase, *Candida antarctica* lipase A, *Candida antarctica* lipase B, *Thermomyces lanuginosus* lipase, *Candida rugose* lipase, and *Mucor miehel* lipase.

3. The process of claim 1, wherein the enzymatic catalyst is immobilized on a solid support.

4. The process of claim 3, wherein the solid support is selected from the group consisting of activated carbon, porous polyamide, porous polyethylene, porous polypropylene, porous phenol formalin resin, porous fluoropolymer, porous acrylic resin and porous polystyrene resin.

5. The process of claim 3 wherein the enzymatic catalyst is *Candida antarctica* lipase B immobilized on a solid support.

6. The process of claim 2, wherein the enzymatic catalyst is immobilized on a solid support.

7. The process of claim 4 wherein the enzymatic catalyst is *Candida antarctica* lipase B immobilized on a solid support.

* * * * *